(12) United States Patent
Yonekawa et al.

(10) Patent No.: US 6,592,533 B1
(45) Date of Patent: Jul. 15, 2003

(54) AIR MASSAGER

(75) Inventors: Mitsuhisa Yonekawa, Kawasaki (JP); Shoji Hoshino, Atsugi (JP); Hiroaki Kobayashi, Hadano (JP)

(73) Assignee: Toshiba Tec Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/458,212

(22) Filed: Dec. 9, 1999

(30) Foreign Application Priority Data

Apr. 14, 1999 (JP) ............................................. 11-106611

(51) Int. Cl.$^7$ ................................................ A61M 9/00
(52) U.S. Cl. ......................................... 601/148; 601/49
(58) Field of Search ................................ 601/148–152, 601/46, 48, 49, 55–58, 76, 77

(56) References Cited

U.S. PATENT DOCUMENTS

| | | | | |
|---|---|---|---|---|
| 1,332,933 A | | 3/1920 | Sylvester | |
| 3,613,671 A | * | 10/1971 | Poor | 128/24 R |
| 3,865,102 A | * | 2/1975 | Birtnell | 128/64 |
| 4,037,591 A | * | 7/1977 | Sarno | 128/33 |
| 4,108,492 A | * | 8/1978 | Kirby | 297/284 |
| 4,136,685 A | * | 1/1979 | Ramey | 128/33 |
| 4,285,544 A | * | 8/1981 | Zapf | 297/218.3 |
| 4,518,200 A | | 5/1985 | Armstrong | |
| 4,761,011 A | | 8/1988 | Sereboff | |
| 4,829,614 A | * | 5/1989 | Harper | 5/436 |
| 4,840,425 A | | 6/1989 | Noble | |
| 5,016,616 A | * | 5/1991 | Hu | 128/32 |
| 5,022,385 A | * | 6/1991 | Harza | 601/149 |
| 5,048,892 A | | 9/1991 | Ledbetter | |
| 5,158,075 A | * | 10/1992 | Howard | 128/41 |
| 5,529,377 A | | 6/1996 | Miller | |
| 5,611,772 A | * | 3/1997 | Fujimoto et al. | 601/149 |
| 5,637,076 A | * | 6/1997 | Hazard et al. | 297/284.6 |
| 5,771,514 A | * | 6/1998 | Wilhoit | 5/644 |
| 5,951,500 A | * | 9/1999 | Cutler | 601/47 |
| 6,209,962 B1 | * | 4/2001 | Sobel et al. | 297/452.17 |

FOREIGN PATENT DOCUMENTS

| | | |
|---|---|---|
| AU | 55387/80 | 2/1980 |
| AU | 52884-98 | 8/1998 |
| DE | 33 00 851 | 7/1984 |
| DE | 36 07 258 | 9/1987 |
| DE | 2 960 3535 | 2/1996 |
| DE | 44 37 394 A1 | 4/1996 |
| EP | 244212 | 11/1987 |
| EP | 0 453 363 A1 | 10/1991 |
| EP | 0 897 684 A | 2/1999 |
| FR | 2549366 | 1/1985 |
| JP | 409122193 | * 5/1997 |
| JP | 410272165 | * 10/1998 |

* cited by examiner

*Primary Examiner*—Justine R. Yu
(74) *Attorney, Agent, or Firm*—Frishauf, Holtz, Goodman & Chick, P.C.

(57) ABSTRACT

In an air massager, a seat, backrest, etc. are provided with cushion units. Each cushion unit includes a pad member, consisting mainly of a fiber-filler, and airbag apparatus put on top of the pad member. The airbag apparatus can be inflated or deflated as air is fed into or discharged from it by means of a pumping device. A compressible distance in the thickness-direction of the pad member is greater than a maximum inflated thickness of the airbag apparatus. The pad member has a thickness, softness, and restorability such that it allows the inflated airbag apparatus to go down into the fiber-filler and incline along a seater's body surface when the airbag apparatus is pressed by the body surface.

6 Claims, 6 Drawing Sheets

AIR MASSAGER

BACKGROUND OF THE INVENTION

The present invention relates to an air massager using airbag apparatus.

A conventional chair-type air massager comprises airbag apparatus located on a user's-body-side surface of a basic structure (chair body) of wood or synthetic resin that is shaped to the user's body. The airbag apparatus is inflated and deflated to massage the user's body by pumping air into or out of the airbag apparatus by means of a pumping device. In order to ease the feeling of stiffness of the airbag apparatus of the massager, a thin urethane foam cushion layer or a cover member made of cloth or leather is laid on, for example, the outer surface of the airbag apparatus.

A mat-type air massager is an alternative known massager in which a plurality of airbags are arranged side by side on a mat body that can be unfolded flat. As air is fed into or discharged from the airbags to inflate or deflate them, the user can be massaged lying on the airbags.

In the case of the conventional chair-type air massager, the shape of the basic structure is made to fit with that of the user's body surface in some measure. If there are wide differences between the basic structure and the body surface, depending on the dimensions or figure of the user's body, however, the basic structure never fits with the user's body, thus failing to ensure a satisfactory massaging force or relaxative effect. Since the conventional airbag apparatus can simply inflate and deflate in the thickness direction of the basic structure, the feeling of stiffness can be eased only limitedly. Thus, the seated user is liable to feel uneasy and find it hard to be relaxed in the massager. Further, the basic structure of the conventional air massager of this chair-type, which is shaped to the user's body surface, entails higher manufacturing cost.

In the case of the mat-type air massager, on the other hand, the individual airbags can simply inflate and deflate in the thickness direction of the mat body. Even if the airbags are arranged according to the figure of a standard user's body, they easily produce an awkward feeling, depending on the body figure of each individual user. In some case, therefore, the user cannot be easily massaged in a fully relaxed state.

BRIEF SUMMARY OF THE INVENTION

Accordingly, the object of the present invention is to provide an air massager capable of giving a user a comfortable, fully relaxed feeling of being surrounded in something and ensuring a satisfactory massaging effect without regard to the figure of the user's body or other variations between individual users.

In order to achieve the above object, an air massager according to the present invention comprises airbag apparatus capable of inflating and deflating and having a massaging surface opposed to a user's body surface, a pumping device for pumping air into or out of the airbag apparatus, a cover member covering the airbag apparatus, and a deformable support member including an airbag support portion for supporting the back side of the airbag apparatus and adapted to allow the airbag apparatus to go down into the airbag support portion and incline along the body surface when the airbag apparatus is pressed by the body surface. When this massager massages the body surface with its airbag apparatus inflated and deflated, the airbag apparatus fits so well with the body surface that the user can enjoy a comfortable feeling of being massaged surrounded in the airbag apparatus. This air massager can fully fit with the user's body without regard to the figure of the user's body as it massages the body, thus ensuring a fantastic massaging effect.

The support member according to the invention is a fiber-filler formed of, for example, an aggregate of a large number of fibers and having restorability. This support member can ensure the user of a fully relaxed comfortable feeling, as well as the aforesaid effect of the invention. In this massager, the airbag apparatus supported by means of the fiber-filler presses the user's body surface using its proper stiffness as it is inflated, so that a satisfactory massaging effect can be obtained. When the massager is not actually used for massaging, the fiber-filler enables it to serve as a relaxative chair that is comfortable to sit in. According to this arrangement, a good feeling of fittedness can be obtained without necessarily using any basic structure (chair body or the like) that fits with the user's body surface, that is, even with use of a roughly shaped basic structure that is easy to manufacture.

In the present invention, the thickness of the fiber-filler is not smaller than a maximum inflated thickness of the airbag apparatus, and preferably, a compressible distance of the fiber-filler is greater than the maximum inflated thickness of the airbag apparatus. When the inflated airbag apparatus is pressed by the user's body surface, according to this arrangement, its massaging surface goes down to the height level of the fiber-filler, and the fiber-filler is compressed to generate proper stiffness. With this arrangement, the relaxative effect of the massager can be improved depending on the thickness of the fiber-filler, and the fiber-filler can be made fully to fit with the user's body.

In the present invention, the fiber-filler may be packed in each of a plurality of bags. With this arrangement, the support member can be made to fit with the body surface more easily. Further, the support member may be formed of a large number of movable grain-fillers packed in a bag. With this arrangement, the support member formed of grain-fillers is deformable and properly stiff, and an improved feeling of fittedness can be obtained as its grain-fillers fill gaps between the massager and the body surface.

The present invention is applicable to a chair-type air massager, which comprises a seat and a backrest provided with the airbag apparatus and the support member, respectively. With this arrangement, the user can be massaged comfortably in a seated state.

The chair-type air massager may further comprise a hassock located in front of the seat and provided with the airbag apparatus and the support member. This massager can massage legs with ease and relaxed state.

The airbag apparatus may include a plurality of airbag elements and a hinge portion connecting the airbag elements for inclining action, whereby the airbag apparatus can be made easily to fit with the user's body surface. With this arrangement, the airbag elements that are separately located corresponding to object regions of the user's body to be massaged can be easily inclined along the body surface by means of the hinge portion, so that the airbag apparatus can be made more easily to fit with the body surface. Besides, the relative positions of the airbag elements can be kept fixed.

The airbag apparatus may be attached to the inner surface of the cover member. According to this arrangement, the cover member and the airbag apparatus are formed integrally with each other, so that the airbag apparatus can be made easily to fit with the user's body surface. Alternatively, the airbag apparatus may be attached to the outer surface of the bag that wraps the fiber-fillers therein. According to this arrangement, the bag and the airbag apparatus are formed integrally with each other, so that the airbag apparatus can be made easily to fit with the user's body surface.

The present invention is also applicable to a mat-type air massager, which comprises a mat body capable of being unfolded flat and including the airbag apparatus and the support member thereon. With this arrangement, the user can lie on the massager comfortably during massaging operation. Further, the support member according to the invention may include a supporting element formed of fiber- or grain-fillers and packed in an airtight bag that is connected with the pumping device. According to this arrangement, the airtight bag, which contains the supporting element therein, serves also as airbag apparatus. Thus, diverse cushioning properties and massaging effects can be obtained by combining the airtight bag and the aforesaid airbag apparatus.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
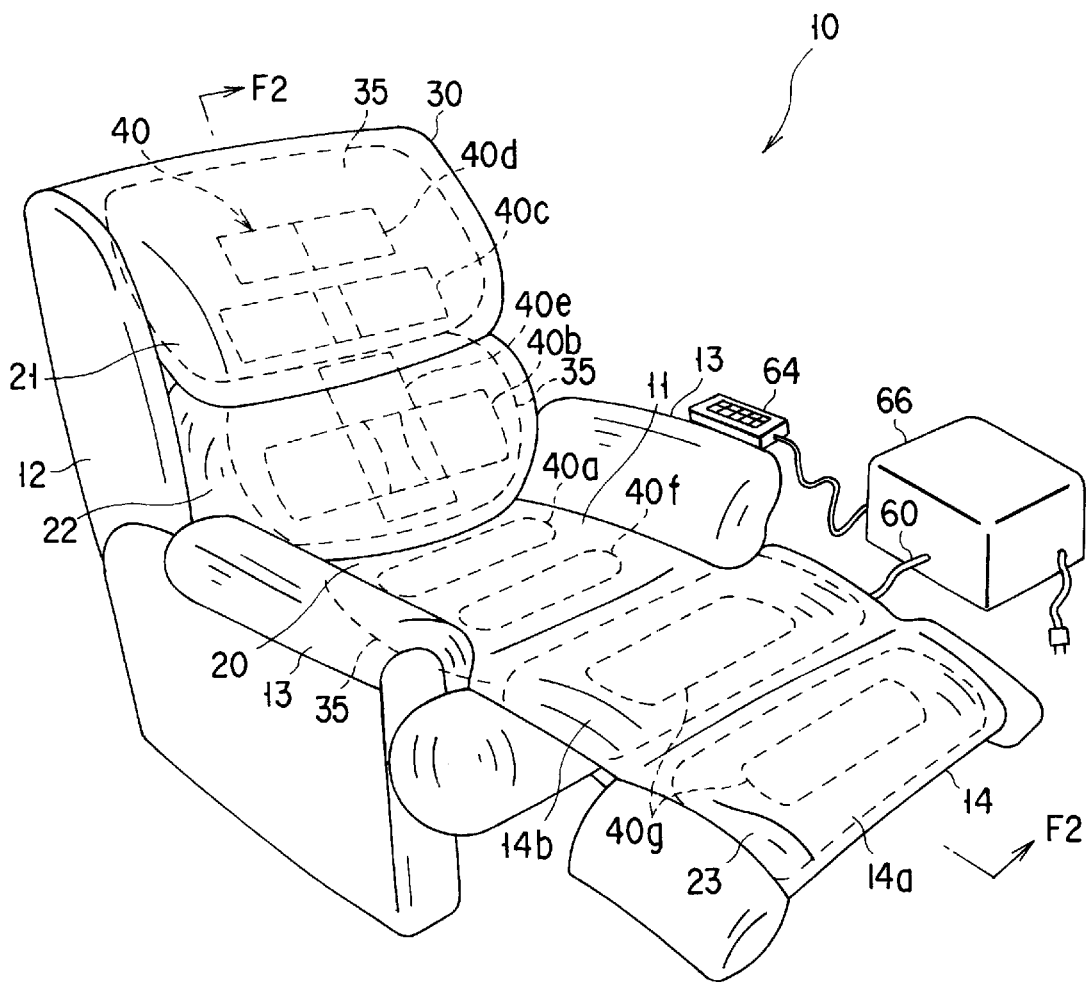
FIG. 1 is a perspective view of a chair-type air massager according to a first embodiment of the present invention.

A chair-type air massager according to a first embodiment of the present invention will now be described with reference to the accompanying drawings of FIGS. 1 to 7.

An air massager 10 according to this embodiment is in the form of a so-called easy chair, comprising a seat 11, backrest 12, armrest 13, hassock 14, etc. The hassock 14 shown in FIG. 1 includes a front portion 14a on the foot side and an intermediate portion 14b on the seat side.

Figure 2:
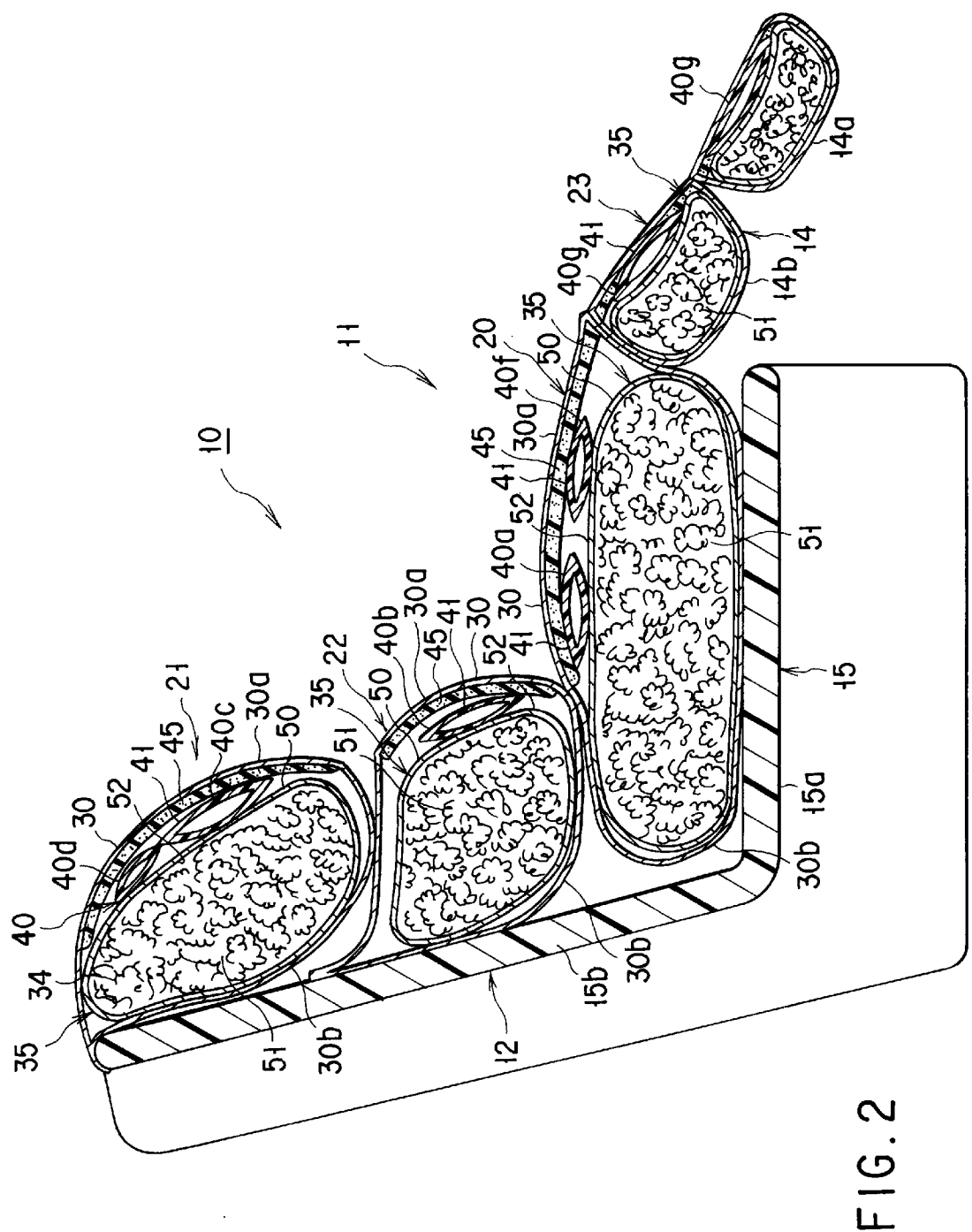
FIG. 2 is a sectional view of the air massager taken along line F2—F2 of FIG. 1.

As shown in FIG. 2, the bottom of the seat 11 and the back of the backrest 12 are provided with a base 15 for use as a chair body that is formed of a material with relatively high stiffness, such as a synthetic resin or wood. The base 15 is composed of a seat base 15a, backrest base 15b, etc. The backrest base 15b may be designed so that the angle of its inclination to the seat base 15a can be changed by means of a reclining mechanism (not shown).

A seat cushion unit 20 is provided on the topside of the seat base 15a. Upper and lower cushion units 21 and 22 are arranged on the front side or seater side of the backrest base 15b. The hassock 14 is also provided with a cushion unit 23.

The cushion units 20 to 23 have a common basic configuration. Each cushion unit includes a cover member 30 in the form of a sewn bag, a pad member 35 for use as a support member 34 held in the cover member 30, airbag apparatus 40 interposed between the cover member 30 and the pad member 35, etc. The obverse of the airbag apparatus 40 that faces a seater M (shown in FIG. 4) across the cover member 30 serves as a massaging surface 41.

The cover member 30 is composed of obverse and reverse covers 30a and 30b that are opposed to the seater M and the base 15, respectively. The obverse cover 30a, which is expected to be touched by a body surface M1 of the seater M, is formed of natural or artificial leather, woven fabric, or any other material that is pleasant to the touch. An openable fastener (not shown) for the pad member 35 is attached to an inconspicuous portion of the cover member 30, e.g., a suitable portion of the reverse cover 30b. A cushion member 45 of, e.g., a thin urethane foam for use as a lining is provided on the back surface of the obverse cover 30a.

The pad member 35 in the cover member 30 is composed of an inner bag 50 of a thin, soft breathable material, such as woven fabric, and a fiber-filler 51 packed in the bag 50. The inner bag 50 is provided with an openable fastener (not shown) for the fiber-filler 51. The obverse side (seater side) of the pad member 35 serves as an airbag support portion 52 for supporting the back surface of the airbag apparatus 40.

Figure 3:
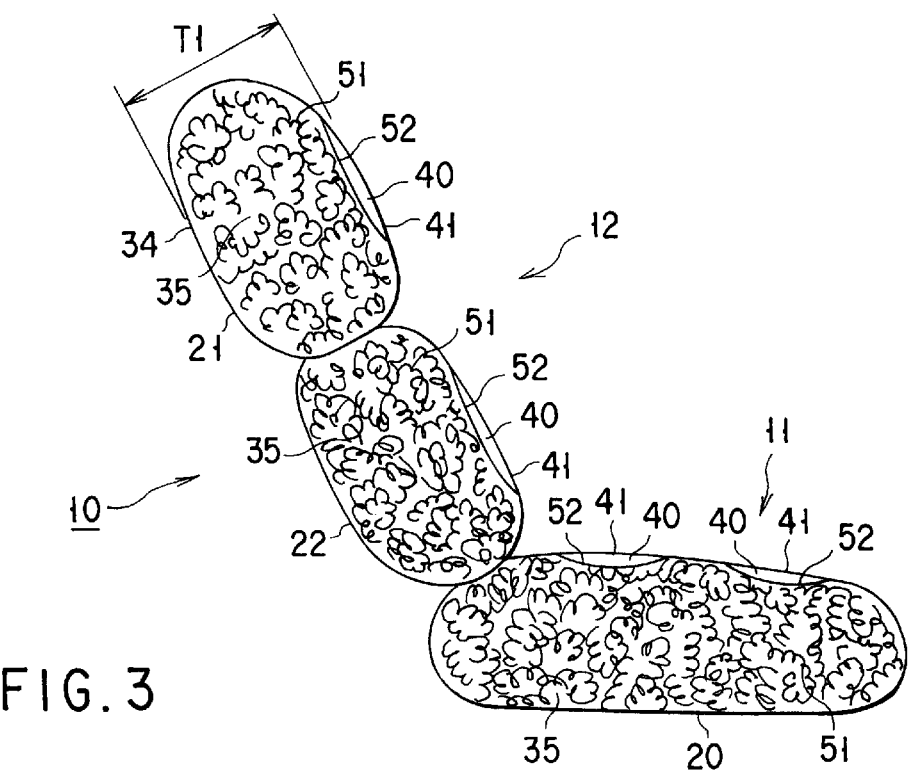
FIG. 3 is a vertical sectional view schematically showing pad members and airbag apparatus of the air massager shown in FIG. 1.

An example of the fiber-filler 51 is formed of an aggregate of a large number of curled polyester fibers, typical synthetic fibers. When no user is seated with the airbag apparatus 40 deflated, as is schematically shown in FIG. 3, a thickness T1 of the pad member 35 is adjusted to 5 cm or more, and preferably to 10 cm or more.

Figure 4:
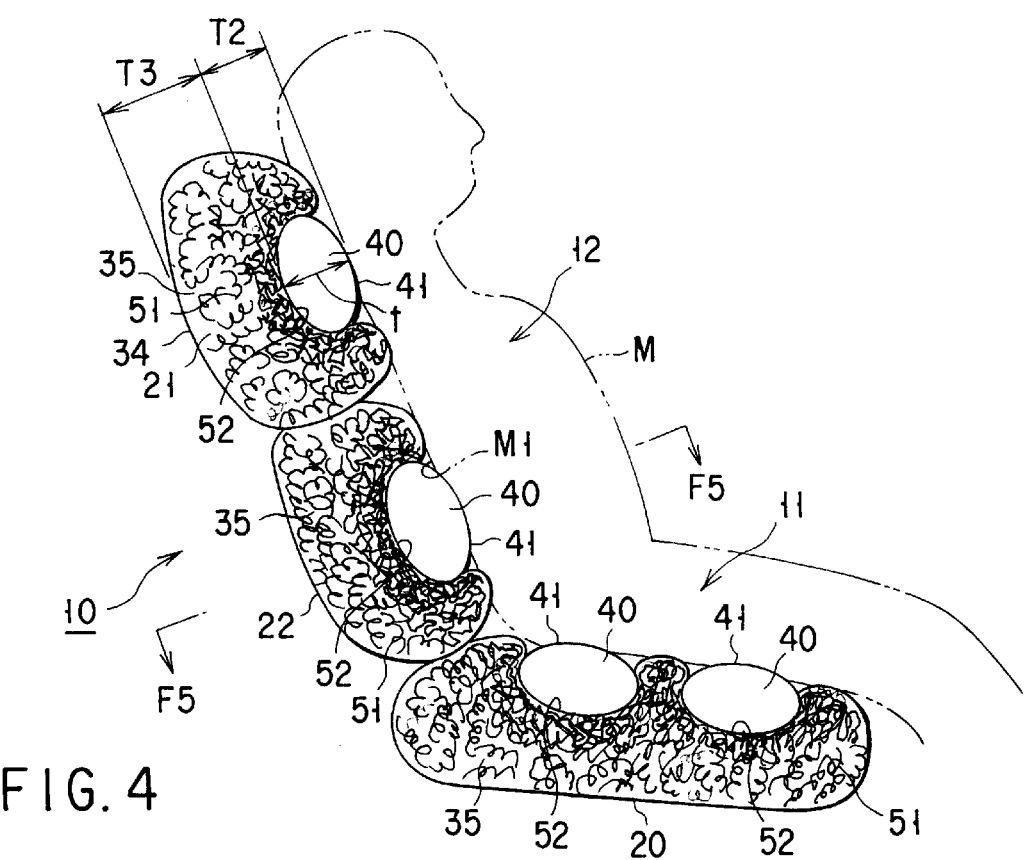
FIG. 4 is a vertical sectional view schematically showing the air massager of FIG. 1 and a user seated therein.

When the seater M is seated in the massager 10 with the airbag apparatus 40 inflated, as shown in FIG. 4, his or her body surface M1 presses the airbag apparatus 40, so that the fiber-filler 51 is compressed and deformed. The fiber-filler 51 is soft and deformable so that it goes down toward the inner part of the airbag support portion 52 to form a local high-density portion, thereby ensuring proper stiffness, when the airbag apparatus 40 is pressed. Nevertheless, the fiber-filler 51 also has proper restorability (resilience) such that it can be restored to its original shape (shown in FIG. 3) when unloaded.

The thickness T1 of the pad member 35 is not smaller than a maximum inflated thickness t of the airbag apparatus 40. Preferably, a compressible distance T2 along thickness-direction of the pad member 35 is greater than the maximum inflated thickness t of the airbag apparatus 40. Thus, when the seater M is seated in the manner shown in FIGS. 4 and 5, the obverse of the airbag apparatus 40, that is, the massaging surface 41, can go down to be substantially flush with the surrounding surface of the pad member 35. In this specification, the compressible distance T2 means the difference between the thickness T1 the pad member 35 has when it is applied with no load and the thickness T3 the pad member 35 has when it is compressed to a maximum degree.

Figure 7:
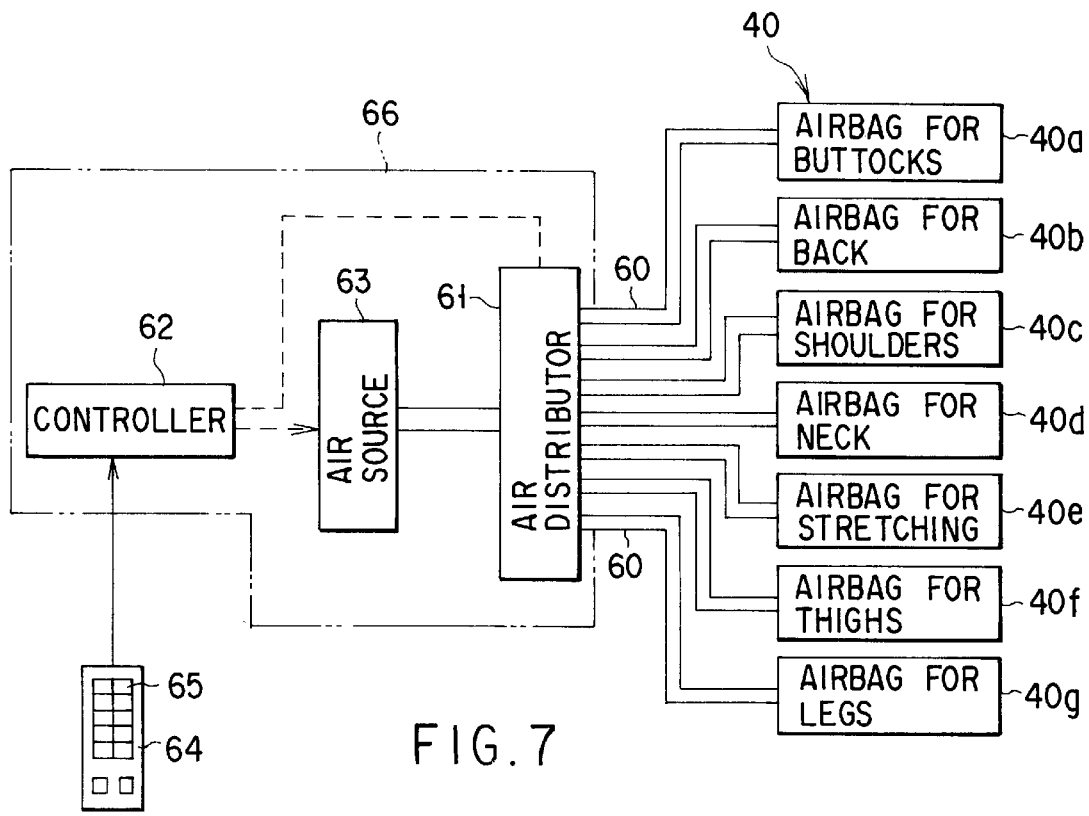
FIG. 7 is a block diagram schematically showing a pumping device and the airbag apparatus of the air massager of FIG. 1.

The airbag apparatus 40 is sandwiched between the obverse cover 30a and the pad member 35. As shown in FIGS. 1 and 7, for example, the airbag apparatus 40 is divided in several parts corresponding to object regions of the seater's body to be massaged, including an airbag 40a for the buttocks, airbag 40b for the back, airbag 40c for the shoulders, airbag 40d for the neck, airbag 40e for stretching, airbag 40f for thighs, airbag 40g for legs, etc. The airbags 40a to 40g take partial charge of massaging for their corresponding regions of the seater's body.

The airbags 40a to 40g are connected to an air distributor 61 (shown in FIG. 7) by means of their corresponding air tubes 60. The air distributor 61 is provided with a selector valve (not shown), such as a rotary valve or solenoid valve. The operation of the selector valve is controlled by means of a controller 62 based on a microcomputer or the like. The airbags 40a to 40g can be inflated alternatively or in regular order by being supplied with compressed air from an air source 63, such as an air pump, as required.

A control panel 64 is connected electrically to the controller 62. A desired one or ones of the airbags 40a to 40g can be inflated or deflated by operating any of switches 65 on the control panel 64. The air tubes 60, air distributor 61, controller 62, air source 63, etc. constitute a pumping device 66 according to the present invention.

In some of the airbags 40a to 40g (represented by the airbag 40c for the shoulders shown in FIG. 6), a plurality of airbag elements 70, parted right and left, can bend in the shape of a V or U around a hinge portion 71 to improve the massaging effect, depending on the regions of the seater's body to be massaged. Thus, these airbags are split airbags each including the airbag elements 70 that are connected for inclining action. For higher inflated-state stability, some airbags, including the airbag 40g for legs, should not be of the split type, preferably.

Figure 6:
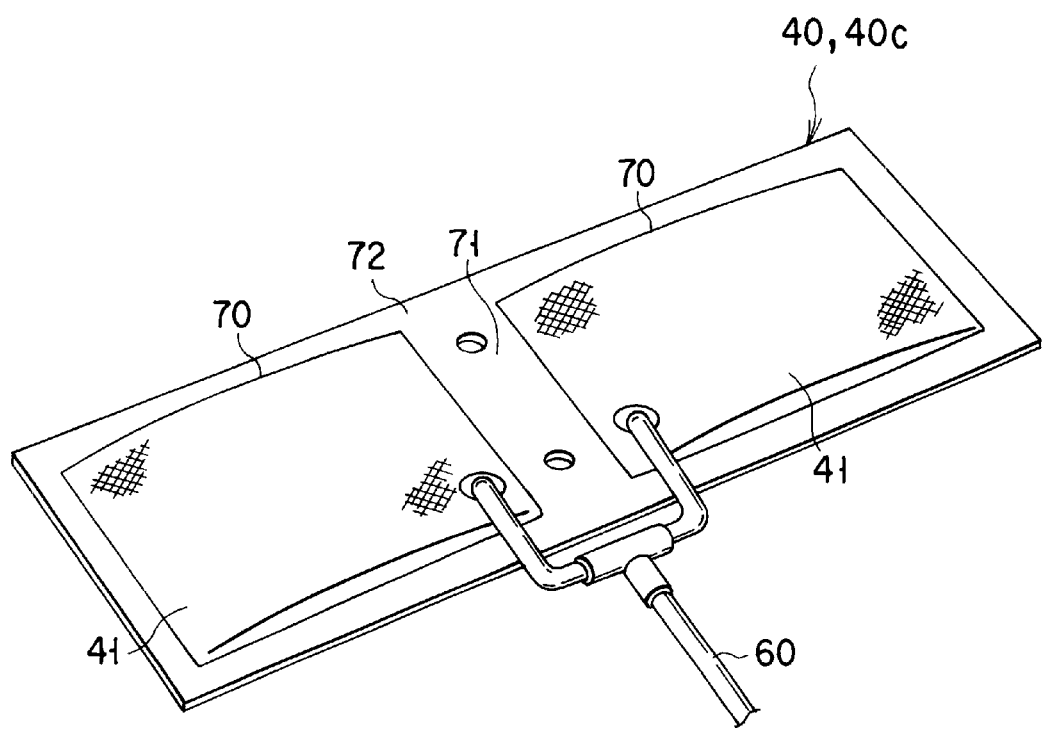
FIG. 6 is a perspective view of an example of an airbag used in the air massager shown in FIG. 1.

As shown in FIG. 6, the airbag 40c includes a plurality of airbag elements 70. In this airbag 40c, the inflatable airbag elements 70 are formed independently of each other on a synthetic resin sheet 72. A thin portion between the airbag elements 70 serves as the deformable or flexible hinge portion 71 (so-called self-hinge). The airbags 40a to 40g may be sewn to the respective inner surfaces of their corresponding cover members 30 or attached to the respective outer surfaces of their corresponding inner bags 50. In either case, the airbags can be easily arranged along the seater's body surface.

The following is a description of the operation of the air massager 10 according to this embodiment.

Figure 5:
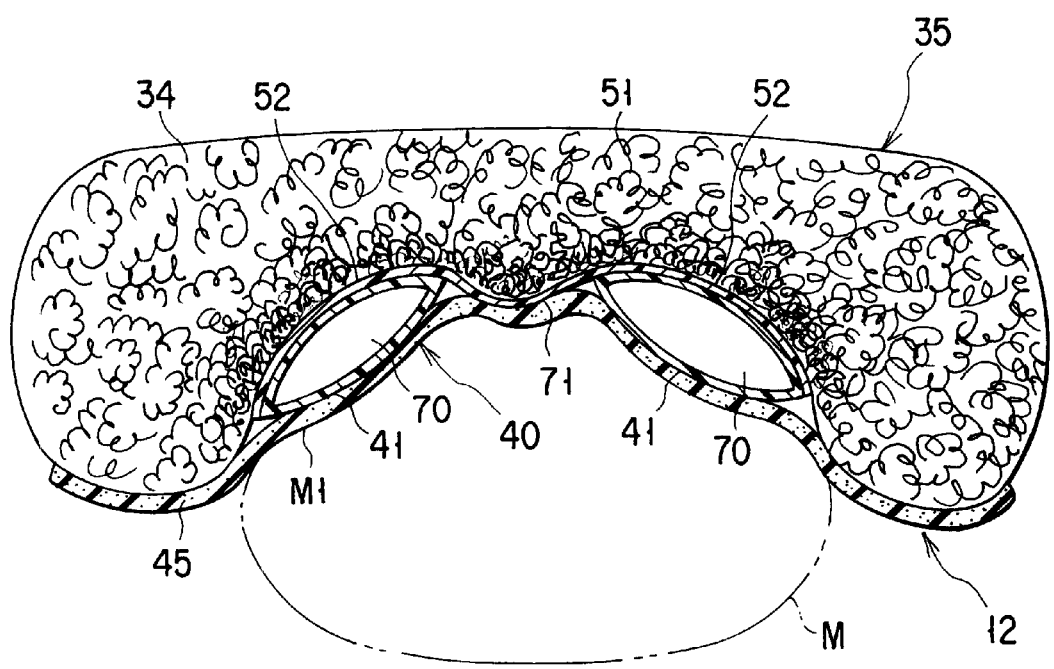
FIG. 5 is a cross-sectional view of the air massager taken along line F5—F5 of FIG. 4.

As shown in FIG. 4, the seater M is seated in the air massager 10 and inflates a desired airbag apparatus 40 (at least one of the airbags 40a to 40g). Thereupon, the airbag apparatus 40 is pressed by the body surface M1 of the seater M, so that it goes down toward the inner part of the airbag support portion 52 within the range of the compressible distance T2 of the fiber-filler 51. As this is done, the fiber-filler 51 is compressed so that its density locally increases. As shown in FIG. 5, moreover, the airbag apparatus 40 inclines along the body surface M1.

Thus, the pad member 35 and the airbag apparatus 40 fit well with the body surface M1 so as to catch the seater M therein. The airbag apparatus 40 massages the seater's body as it is repeatedly inflated and deflated. Accordingly, the performance of the airbag to hold and fit the body surface M1 during the massaging operation is improved, so that effective massaging can be carried out in a fully relaxed state. Since the pad member 35 is deformable, the air massager 10 can be used as an ordinary easy chair that is comfortable to sit in and can make the seater relaxed even when the massaging operation is stopped. When the airbag apparatus 40 is inflated, the airbag support portion 52 of the fiber-filler 51 is compressed to generate proper stiffness, thereby ensuring a satisfactory massaging effect.

According to the embodiment described above, the pad member 35 that is formed of the inner bag 50 and the fiber-filler 51 is used as the support member. Alternatively, however, the support member may be formed of, for example, a large number of grain-fillers such as synthetic resin pellets that are movably packed in a flexible bag. Alternatively, moreover, the support member may be formed of a synthetic resin foam that has deformability and proper restorability.

Figure 8A:
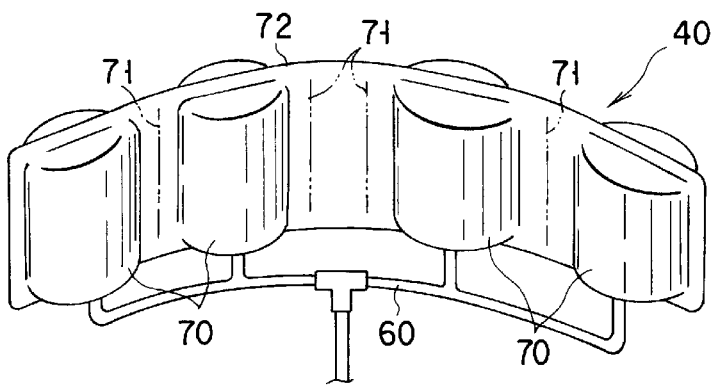
FIG. 8A is a perspective view of airbag apparatus according to a second embodiment of the invention.

FIG. 8A shows a second embodiment of the invention, in which airbag apparatus 40 includes two or more airbag elements 70. In this airbag apparatus 40, the respective flanks of the airbag elements 70 are connected to one another by means of hinge portions 71, individually, so that they can easily bend along the seater's body surface. Each airbag element 70 is connected with an air tube 60, which is similar to each air tube 60 according to the foregoing embodiment, whereby the element 70 can be inflated and deflated.

Figure 8B:
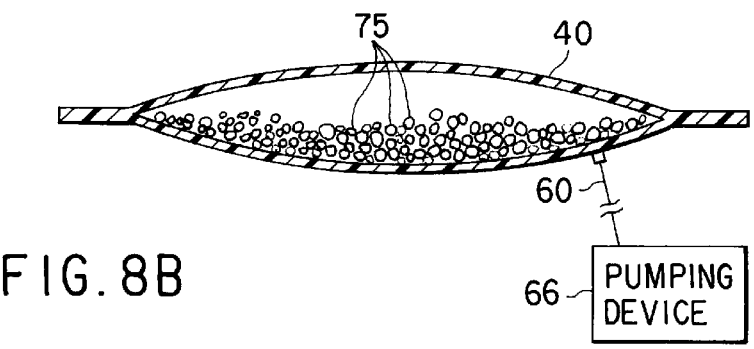
FIG. 8B is a sectional view of airbag apparatus according to a third embodiment of the invention.

According to a third embodiment shown in FIG. 8B, a large number of grain-fillers 75 are packed in airbag apparatus 40. The grain-fillers 75 may be pellets or pieces of a synthetic resin or seeds of a plant, for example. If air in the airbag apparatus 40 is discharged by means of a pumping device 66, according to this embodiment, the airbag apparatus 40 becomes deflated, and the grain-fillers 75 are fixed to one another, so that the stiffness of the airbag apparatus 40 increases. If air is fed into the airbag apparatus 40 by means of the pumping device 66, on the other hand, the airbag apparatus 40 inflates, so that its stiffness lowers. The massaging effect can be enhanced by inflating and deflating the airbag apparatus 40 in this manner.

Figure 9A:
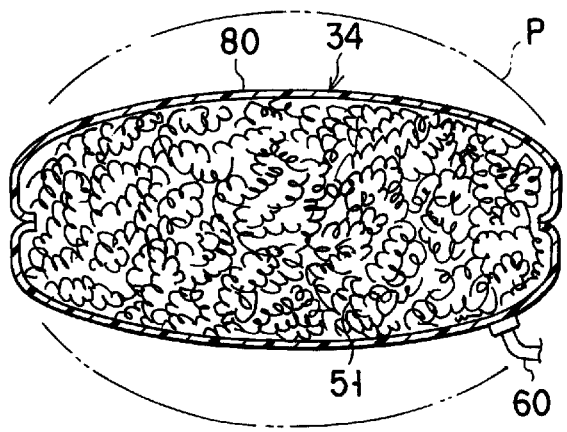
FIG. 9A is a sectional view of a fiber-filler-packed sealed bag according to a fourth embodiment of the invention.

FIG. 9A shows a support member 34 according to a fourth embodiment of the invention. In this support member 34, an airtight sealed bag 80 is packed with a fiber-filler 51, which is similar to the one according to the first embodiment. An air tube 60 of a pumping device is connected to the sealed bag 80. The bag 80 can be inflated, as indicated by two-dot chain line P, by being supplied with air. Diverse cushioning properties and massaging effects can be obtained by combining the sealed bag 80 and the airbag apparatus 40.

Figure 9B:
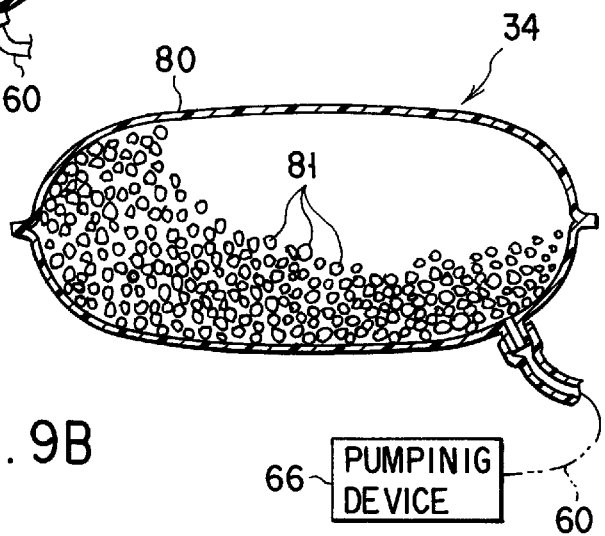
FIG. 9B is a sectional view of a grain-filler-packed sealed bag according to a fifth embodiment of the invention.

FIG. 9B shows a support member 34 according to a fifth embodiment of the invention. This support member 34 comprises a sealed bag 80 and a large number of grain-fillers 81 therein. A pumping device 66 is connected to the bag 80 by means of an air tube 60. The grain-fillers 81 may be pellets or pieces of a synthetic resin or seeds of a plant, for example. If air in the bag 80 is discharged by means of the pumping device 66, according to this embodiment, the bag 80 becomes deflated, and the grain-fillers 81 are fixed to one another, so that the stiffness of the support member 34 increases. If air is fed into the bag 80, on the other hand, the stiffness of the support member 34 lowers.

Figure 10:
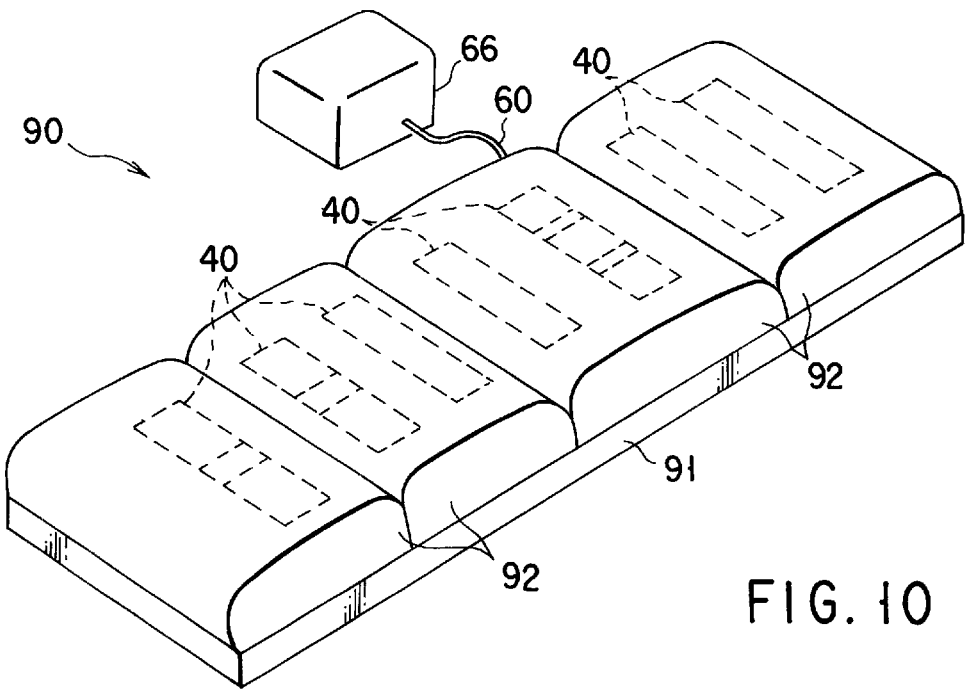
FIG. 10 is a perspective view of a mat-type air massager according to a sixth embodiment of the invention.

According to a sixth embodiment shown in FIG. 10, the present invention is applied to a mat-type air massager 90.

In this massager 90, a plurality of cushion units 92 are arranged on a mat body 91 that can be unfolded flat. Like each of the cushion units 20 to 22 described in connection with the first embodiment, each unit 92 includes a support member (e.g., fiber-filler 51) according to the present invention and airbag apparatus 40. For the constructions, functions, and effects of other elements, this embodiment resembles the first embodiment. Therefore, common reference numerals are used to designate portions that are common to the first and sixth embodiments, and a description of those portions is omitted.

It is to be understood that the elements that constitute the present invention, such as the airbag apparatus, support member, pumping device, cover member, etc., may be suitably modified in carrying out the invention represented by the embodiments described herein.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An air massager comprising:

a base having a seat and a backrest;

an airbag apparatus disposed on the backrest and being capable of inflating and deflating and having a massaging surface adapted to be opposed to a user's body, said airbag apparatus comprising a plurality of airbag elements separated into right and left groups with respect to a center of the user's body, and a hinge portion which connects the right and left groups of airbag elements, said hinge portion being located at a center in a width direction of the backrest, and said airbag apparatus being bendable in one of a U shape and V shape around the hinge portion;

a pumping device for pumping air into or out of the airbag apparatus;

a cover member covering the airbag apparatus; and a deformable support member including an airbag support portion for supporting a back side of the airbag apparatus;

wherein said deformable support member comprises a fiber-filler formed of an aggregate of a large number of fibers and having restorability;

wherein said deformable support member is adapted to enable the airbag apparatus to be depressed into the airbag support portion, and the airbag apparatus is bendable such that the hinge portion retreats backward from both end portions of the airbag apparatus and inclines along the user's body when the airbag apparatus is inflated and pressed by the user's body; and wherein said fiber-filler is packed in each of a plurality of bags arranged along the user's body.

2. An air massager according to claim 1, wherein a compressible distance in a thickness-direction of said deformable support member is greater than the maximum inflated thickness of the airbag apparatus, so that the massaging surface of the inflated airbag apparatus is enabled to be compressed to be substantially flush with a surrounding surface of the support member when the airbag apparatus is pressed by the user's body.

3. An air massager according to claim 1, further comprising a hassock located in front of the seat and provided with the airbag apparatus and the support member.

4. An air massager according to claim 1, wherein said airbag apparatus is attached to an inner surface of the cover member.

5. An air massager according to claim 1, wherein said airbag apparatus is attached to an outer surface of the bags.

6. An air massager comprising:

an airbag apparatus capable of inflating and deflating and having a massaging surface adapted to be opposed to a user's body, said airbag apparatus comprising a plurality of airbag elements separated into right and left groups with respect to a center of the user's body;

a pumping device for pumping air into or out of the airbag apparatus;

a cover member covering the airbag apparatus;

a deformable support member including an airbag support portion for supporting a back side of the airbag apparatus, said deformable support member being adapted to enable the airbag apparatus to be depressed into the airbag support portion and incline along the user's body when the airbag apparatus is pressed by the user's body; and a mat body capable of being unfolded flat and having the airbag apparatus and the support member provided thereon;

wherein said deformable support member comprises a fiber-filler formed of an aggregate of a large number of fibers and having restorability; and wherein said fiber-filler is packed in each of a plurality of bags arranged along the user's body.

\* \* \* \* \*